(12) United States Patent
Wu et al.

(10) Patent No.: US 8,853,271 B2
(45) Date of Patent: Oct. 7, 2014

(54) METHOD FOR INHIBITING ACTIVITY AND/OR EXPRESSION OF MATRIX METALLOPROTEINASE, INHIBITING PHOSPHORYLATION OF MITOGEN-ACTIVATED PROTEIN KINASE, AND/OR PROMOTING EXPRESSION OF COLLAGEN USING TORMENTIC ACID (75) Inventors: Jin-Bin Wu, Taichung (TW); Wen-Chuan Lin, Taichung (TW); Hui-Ya Ho, Taichung (TW); Sze-Ying Chen, Taichung (TW)

(73) Assignee: China Medical University, Taichung (TW)

( * ) Notice: Subject to any disclaimer, the term of this patent is extended or adjusted under 35 U.S.C. 154(b) by 615 days.

(21) Appl. No.: 12/955,336

(22) Filed: Nov. 29, 2010

(65) Prior Publication Data
US 2012/0059059 A1   Mar. 8, 2012

(30) Foreign Application Priority Data

Sep. 3, 2010  (TW) ............................... 99129879 A (51) Int. Cl.
| A61K 31/191 | (2006.01) |
| A61P 17/00 | (2006.01) |
| A61Q 19/08 | (2006.01) |
| A61K 8/365 | (2006.01) |
| C07C 61/29 | (2006.01) |
| A61K 31/19 | (2006.01) |
| A61K 8/63 | (2006.01) |

(52) U.S. Cl.
CPC . *A61K 8/63* (2013.01); *A61Q 19/08* (2013.01); *A61K 31/19* (2013.01); *A61K 2800/782* (2013.01)
USPC .......................................... 514/557; 562/498

(58) Field of Classification Search
USPC ........................................... 514/557; 562/498
See application file for complete search history.

(56) References Cited

U.S. PATENT DOCUMENTS

2006/0134229 A1* 6/2006 Li et al. .......................... 424/725
2011/0086088 A1* 4/2011 Berry ............................. 424/450

FOREIGN PATENT DOCUMENTS

| DE | 103 59 153 | 7/2005 |
| JP | 3188019 | 8/1991 |
| JP | 2001 213778 | 8/2001 |
| WO | WO 2006/010147 | 1/2006 |
| WO | WO 2011/126539 | 10/2011 |

OTHER PUBLICATIONS

Qin Zhang & Zai Chang & Qiang Wang, Ursane Triterpenoids Inhibit Atherosclerosis and Xanthoma in LDL Receptor Knockout Mice, Cardiovasc Drugs Ther (2006) 20: 349-357.*

Gabriele A.M. Plenz, Mario C. Deng, Horst Robenek, Wolfgang Volker, Vascular collagens: spotlight on the role of type VIII collagen in atherogenesis, Atherosclerosis 166 (2003) 1-11.*
Sze-Ying Chen, "Effects of Triterpenes Extracted from Suspension *Eriobotrya japonica* cell on Ultraviolet B-induced Skin Aging", Jul. 17, 2010, Education Thesis Dissertation Service (TW), http://etds-lib.cmu.edu.tw, Aug. 3, 2012.
Ramachandran S. et al., "Modulation of UVB-induced Oxidative Stress by Ursolic Acid in Human Blood Lymphocytes, Asian Journal of Biochemistry", vol. 3, No. 1, 2008, pp. 11-18.
Taniguchi S et al., "Production of bioactive triterpenes by *Eriobotrya japonica* calli", Phytochemistry, Feb. 1, 2002, vol. 59, No. 3, pp. 315-323.
Chen et al., "Effects of Triterpenes Extracted from *Eriobotrya japonica* Callus Tissue Cultures on Ultraviolet B-induced Skin Aging" The 25th Joint Annual Conference of Biomedical Science, Biomedical Science, 2010.
Dannenbert et al., "Histochemical demonstration of hydrogen peroxide production by leukocytes in fixed-frozen tissue sections of inflammatory lesions", Journal of Leukocyte Biology, vol. 56, Oct. 1994, pp. 436-443.
Kim et al., "Effects of ginseng saponins isolated from red ginseng on ultraviolet B-induced skin aging in hairless mice", European Journal of Pharmacology 602 (2009) pp. 148-156.
Moon et al., "The effect of erythrodiol-3-acetate on the expressions of matrix metalloproteinase-1 and type-1 procollagen caused by ultraviolet irradiated cultured primary old aged human skin fibroblasts", *Phytomedicine*, vol. 13, 2006, pp. 707-711.
Office Action from the European Patent Office in the counterpart EP application 11167430.5-2112.

* cited by examiner

*Primary Examiner* — Kendra D Carter
*Assistant Examiner* — Jason A Deck
(74) *Attorney, Agent, or Firm* — Greer, Burns & Crain, Ltd.

(57) ABSTRACT

A method for inhibiting the activity of matrix metalloproteinase (MMP), inhibiting the expression of matrix metalloproteinase, inhibiting the phosphorylation of mitogen-activated protein kinase (MAPK), and/or promoting the expression of collagen in a mammal is provided. The method comprises administrating to the mammal an effective amount of an active component selected from a group consisting of a compound of formula (I), a pharmaceutically acceptable salt of the compound, a pharmaceutically acceptable ester of the compound, and combinations thereof:

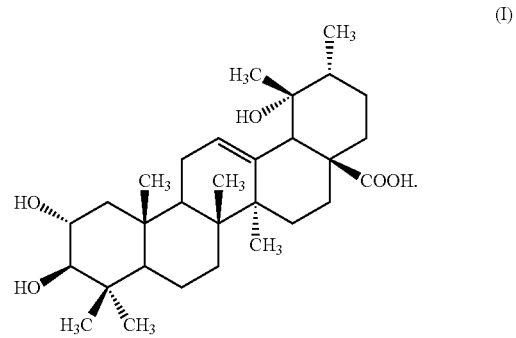

(I)

16 Claims, 10 Drawing Sheets
(5 of 10 Drawing Sheet(s) Filed in Color)

METHOD FOR INHIBITING ACTIVITY AND/OR EXPRESSION OF MATRIX METALLOPROTEINASE, INHIBITING PHOSPHORYLATION OF MITOGEN-ACTIVATED PROTEIN KINASE, AND/OR PROMOTING EXPRESSION OF COLLAGEN USING TORMENTIC ACID

CROSS-REFERENCES TO RELATED APPLICATIONS

This application claims the benefit of Taiwan Patent Application No. 099129879, filed on Sep. 3, 2010, in the Taiwan Intellectual Property Office, the disclosure of which is incorporated herein in its entirety by reference.

BACKGROUND OF THE INVENTION

1. Field of the Invention

The present invention relates to the uses of tormentic acid in the inhibition of the activity of matrix metalloproteinase (MMP), inhibition of the expression of matrix metalloproteinase, inhibition of the phosphorylation of mitogen-activated protein kinase (MAPK), and/or promotion of the expression of collagen, especially in the improvement, repair, and/or care of skin.

2. Descriptions of the Related Art

Natural human aging processes include skin flaccidity, wrinkle formation and skin darkening, which gradually appear with aging. The layers of skin from top to bottom are the epidermis, dermis, and hypodermis. The causes of skin aging can be classified by endogenous and exogenous factors. Endogenous aging is a natural aging process of the human body, including cell apoptosis, hormone decrease, and weakened immunity. The decrease of hormone secretion may slow the metabolism of skin and gradually reduce the production of collagen and elastin because of the deterioration of the function of fibroblasts in the dermis. As a result, the connective tissues in the dermis degenerate, leading to flaccidity, and even wrinkling of the skin. Furthermore, the degeneration of connective tissues in the dermis may decrease the water storage (holding) function of the skin, leading to skin dryness and water deficiency, etc.

Exogenous aging is caused by extrinsic factors, such as sunshine, pollution, free radicals, and smoking. The main factor that damages the skin most and accelerates skin aging is ultraviolet (UV) rays from the sun. Depending on the wavelength, ultraviolet rays can be classified into long wavelength UV (UVA), medium wavelength UV (UVB), and short wavelength UV (UVC). Ultraviolet rays that people are most exposed to in daily life are UVA and UVB, which may cause erythema, sunburns, damage to the deoxyribonucleic acid (DNA) in skin cells, abnormality of the skin immune system, and skin cancer. The aging phenomenon caused by ultraviolet rays is called "photo-aging," which may lead to an increase of matrix metalloproteinase (MMP) in the dermis via the phosphorylation of the mitogen-activated protein kinase (MAPK) pathway. Matrix metalloproteinase may decompose collagen in the skin. Without the support of collagen, the skin becomes flaccid, and cuticula may overgrow, leading to darkened and wrinkled skin.

Animal collagen that is currently known can be classified approximately into 21 types. Different kinds of collagen exist in different tissues. Out of all collagen in skin tissues, Type I collagen is the most abundant (80% of skin collagen) and has the most functions. Type III collagen comprises about 20% of the skin collagen. Fibroblasts in the dermis mainly produce Type I collagen and Type III collagen for the skin.

As described above, matrix metalloproteinase may decompose collagen and reduce the collagen content in the skin. Accordingly, if the MAPK Pathway or the activity and/or expression of matrix metalloproteinase in cells can be inhibited, the effects of improving/caring for skin quality can be achieved.

The inventors of the present invention found that tormentic acid has excellent effects of inhibiting the activity of matrix metalloproteinase, inhibiting the expression of matrix metalloproteinase, inhibiting the phosphorylation of mitogen-activated protein kinase, and/or promoting the expression of collagen, and thus it can be used for improving, repairing, and/or caring for the skin.

SUMMARY OF THE INVENTION

The primary objective of this invention is to provide a method for inhibiting the activity of matrix metalloproteinase (MMP), inhibiting the expression of matrix metalloproteinase, inhibiting the phosphorylation of mitogen-activated protein kinase (MAPK), and/or promoting the expression of collagen in a mammal, comprising administrating to the mammal an effective amount of an active component selected from a group consisting of a compound of formula (I), a pharmaceutically acceptable salt of the compound, a pharmaceutically acceptable ester of the compound, and combinations thereof:

Another objective of this invention is to provide a pharmaceutical composition for inhibiting the activity of matrix metalloproteinase, inhibiting the expression of matrix metalloproteinase, inhibiting the phosphorylation of mitogen-activated protein kinase, and/or promoting the expression of collagen, which comprises an effective amount of the aforesaid active component.

Yet a further objective of this invention is to provide the use of the aforesaid active component in the manufacture of a medicament for inhibiting the activity of matrix metalloproteinase, inhibiting the expression of matrix metalloproteinase, inhibiting the phosphorylation of mitogen-activated protein kinase, and/or promoting the expression of collagen.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DESCRIPTION OF THE PREFERRED EMBODIMENT

Unless otherwise stated herein, the terms "a (an)", "the" or the like used in this specification (especially in the Claims hereinafter) shall be understood to encompass both the singular form and the plural form.

The present invention relates to a method for inhibiting the activity of matrix metalloproteinase (MMP), inhibiting the expression of matrix metalloproteinase, inhibiting the phosphorylation of mitogen-activated protein kinase (MAPK), and/or promoting the expression of collagen in a mammal, comprising administrating to the mammal an effective amount of an active component selected from a group consisting of a compound of formula (I), a pharmaceutically acceptable salt of the compound, a pharmaceutically acceptable ester of the compound, and combinations thereof:

(I)

The method of the present invention has the effects of inhibiting the activity of matrix metalloproteinase and inhibiting the expression of matrix metalloproteinase, and may prevent or decrease the destruction of collagen. Matrix metalloproteinase can be classified into collagenase, stromelysin, gelatinase, matrilysin, transmembrane type-MMP, etc. Common matrix metalloproteinase includes matrix metalloproteinase-1 (MMP-1), matrix metalloproteinase-2 (MMP-2), matrix metalloproteinase-3 (MMP-3), matrix metalloproteinase-7 (MMP-7), matrix metalloproteinase-8 (MMP-8), matrix metalloproteinase-9 (MMP-9), matrix metalloproteinase-10 (MMP-10), matrix metalloproteinase-11 (MMP-11), matrix metalloproteinase-12 (MMP-12), matrix metalloproteinase-13 (MMP-13), matrix metalloproteinase-14 (MMP-14), etc. In particular, the method of the present invention can effectively inhibit the formation (or expression) of matrix metalloproteinase-1 (MMP-1). MMP-1 is also called collagenase-1, which belongs to the collagenase family. Other names for MMP-1 include tissue collagenase or fibroblast-type collagenase.

In addition to the effects of inhibiting the activity and/or expression of matrix metalloproteinase, the method of the present invention also has the effects of inhibiting the phosphorylation of mitogen-activated protein kinase, and especially has the effects of inhibiting the phosphorylation of c-Jun N-terminal Kinase (JNK), extracellular signal-regulated protein kinase (ERK), and p38 protein. As described above, the phosphorylation of mitogen-activated protein kinase may increase the amount of matrix metalloproteinase in the dermis, which further increases the opportunity of the decomposition of collagen, and decreases the collagen content in the skin accordingly.

Because the method of the present invention has the effects of (1) directly inhibiting the activity and/or expression of matrix metalloproteinase, and (2) indirectly inhibiting the expression of matrix metalloproteinase by inhibiting the phosphorylation of mitogen-activated protein kinase, it may significantly decrease the decomposition of collagen in the skin, thereby increasing the collagen content, especially the content of Type I collagen, and thus may effectively improve, repair, and/or care for skin. For example, the method of the present invention may have the effects of anti-aging, anti-photo-aging, reducing skin wrinkling, improving skin quality and skin flaccidity, promoting wound healing, etc.

The compound of formula (I) (i.e., tormentic acid) can be prepared by a method comprising the following steps. Cultured cells of Eriobotrya japonica Lindl. leaves were extracted with 95 vol % ethanol. The extract was filtrated with a filter paper, and the filtrate was collected and vacuum concentrated to obtain a concentrate. The concentrate was then dissolved with 50 vol % methanol and filtrated with a filter paper, and an insoluble portion was collected. Thereafter, the insoluble portion was dissolved with 85 vol % methanol and filtrated with a filter paper. The filtrate was collected and vacuum concentrated to obtain an extract of Eriobotrya japonica Lindl. leaf cells, which contains a sufficient amount of the compound of formula (I). Finally, the extract was purified with a high performance liquid chromatography (HPLC) instrument to acquire the compound of formula (I).

The present invention also provides a pharmaceutical composition for inhibiting the activity of matrix metalloproteinase, inhibiting the expression of matrix metalloproteinase, inhibiting the phosphorylation of mitogen-activated protein kinase, and/or promoting the expression of collagen, which comprises an effective amount of the active component selected from a group consisting of the compound of formula (I), the pharmaceutically acceptable salt of the compound, the pharmaceutically acceptable ester of the compound, and combinations thereof.

The pharmaceutical composition of the present invention can be of any suitable form without particular limits. For example, the pharmaceutical composition can be in a form of emulsion, cream, or gel for external use, such as a skin care product, cosmetic, etc. The pharmaceutical composition can also be prepared in the form of food for swallowing or drinking, such as health foods, beauty drinks, etc. Furthermore, the pharmaceutical composition can be of a common pharmaceutical form, such as a tablet, capsule, granule, powder, fluid extract, solution, syrup, suspension, emulsion, tincture, intravenous injection, powder injection, suspension injection, powder-suspension injection, etc.

The dosage of the pharmaceutical composition of the present invention may be adjusted according to the age of the treated subject and the purpose of the application (such as reducing skin wrinkles or promoting wound healing), and the usage frequency may also be optionally adjusted. Other components and content thereof are dependent on the final form of the pharmaceutical composition. For instance, when the pharmaceutical composition is prepared as a skin care product, any suitable and appropriate amount of emulsion, perfume, and other active components for improving skin quality may be added therein. In general, any component can be added in the pharmaceutical composition, as long as it has no adverse influence on the effects of the compound of formula (I).

The present invention also provides the use of the aforesaid active component (i.e., the compound of formula (I), the pharmaceutically acceptable salt of the compound, the pharmaceutically acceptable ester of the compound, or combinations thereof) in the manufacture of a medicament for inhibiting the activity of matrix metalloproteinase, inhibiting the expression of matrix metalloproteinase, inhibiting the phosphorylation of mitogen-activated protein kinase, and/or promoting the expression of collagen. The medicament can be used for improving, repairing, and/or caring for skin, and especially can be used for anti-photo-aging. In addition, the medicament especially can be used for inhibiting the activity and/or expression of MMP-1, and/or promoting the expression of Type I collagen.

Hereinafter, the present invention will be further illustrated with reference to the following examples. However, these examples are only provided for illustration purposes, but not to limit the scope of the present invention.

EXAMPLE

Example 1

Preparation of Tormentic Acid (the Compound of Formula (I)

(1) Establishment of Aseptic *Eriobotrya japonica* Lindl Seedlings

Seeds from mature *Eriobotrya japonica* Lindl. in an orchard at Toubiankeng, Taichung county, Taiwan were collected. Then, the seeds were rinsed for 30 minutes, and were soaked in 70% ethanol for about 1 minute. Furthermore, the seeds were soaked in a 1% sodium chlorate solution with 0.01% Tween 20, and placed in an ultrasonic vibrator. After surface disinfecting for about 15 minutes, the seeds were placed on a laminar airflow bench. The seeds were then rinsed with sterile water three to four times, and were cultivated on an MS medium (Murashige-Skoog medium) containing 30 g/L sucrose. After two to three weeks, the seeds began to germinate, and the leaves of the seedlings were collected two months after germination to be the testing materials.

(2) Inducement of Callus Tissue

A leaf of the seedlings was cut for about 0.3 cm, and was transferred to a solid medium (MS basic formula comprising 2.5 ppm 6-benzyladenine (BA), 1 ppm α-naphthaleneacetic acid (NAA), 3% (30 g/L) sucrose, and 0.3% (3 g/L) gelrite) for culture. After one month, light yellow callus tissues were grown from the cut wound.

(3) Cultivation of *Eriobotrya japonica* Lindl. Leaf Cells

Sixty gram of light yellow callus tissues (which may differentiate into new *Eriobotrya japonica* Lindl. leaf cells) as described above were taken and sieved by a 590 μm sieve to separate the callus tissue cells into a specific size. Then, the sieved callus tissue cells were transferred into a bioreactor (BioFlo110 Bioreactor, New Brunswick Scientific, America) containing 4,000 ml culture broth (MS basic formula comprising 2.5 ppm BA, 1 ppm NAA, and 3% (30 g/L) sucrose) for culture (culture condition: the aeration rate was 0.3 v.v.m. (the gas volume flow per unit of liquid volume per minute); stirring rate was 40 rpm; temperature was 24 to 26° C.). Every time when the callus tissues were sub-cultured with fresh culture broth once every ten days, 500 ml original cell suspension (i.e., culture broth) remained, and 4,500 ml fresh culture broth was added thereto. The remaining 4,500 ml original culture broth (including about 320 g cells) was transferred into a bioreactor (a stainless steel bottle of 30 L volume) with 25.5 L culture broth (MS basic formula comprising 2.5 ppm BA, 1 ppm NAA, and 3% (30 g/L) sucrose). Then, 1 ppm of a raffinate of *Eriobotrya japonica* Lindl. leaf cells was added to the culture broth to continue the culture of the differentiated *Eriobotrya japonica* Lindl. leaf cells. The culture was terminated after 18 days.

(4) Preparation of the Raffinate of the *Eriobotrya japonica* Lindl. Leaf Cells

The cultured *Eriobotrya japonica* Lindl. leaf cells were obtained from an individual batch culture and dried (about 5,400 g before dried; about 320 g after dried). The cells were reflux extracted thrice with 95 vol % ethanol. The obtained extract was filtered with a filter paper, and the filtrate was collected and vacuum concentrated to obtain a concentrate. Then, the concentrate was dissolved twice with 50 vol % methanol, and was filtered with a filter paper to obtain an insoluble portion. Furthermore, the insoluble portion was dissolved thrice with 85 vol % methanol and filtrated with a filter paper, and an insoluble portion was collected to obtain the raffinate of the *Eriobotrya japonica* Lindl. leaf cells.

(5) Preparation of the Extract of the *Eriobotrya japonica* Lindl. Leaf Cells

Cultured *Eriobotrya japonica* Lindl. leaf cells were obtained from an individual culture batch and dried at 60° C. (about 5,400 g before dried; about 320 g after dried). The cells were reflux extracted thrice with 10 L 95 vol % ethanol. The obtained extract was filtered with a filter paper, and the filtrate was collected and vacuum concentrated to obtain a concentrate. Then, the concentrate was dissolved twice with 5 L 50 vol % methanol, and was filtered with a filter paper to obtain an insoluble portion. Furthermore, the insoluble portion was dissolved thrice with 10 L 85 vol % methanol and filtrated with a filter paper, and the filtrate was collected and vacuum concentrated to obtain about 53 g white powder of an extract of the *Eriobotrya japonica* Lindl. leaf cells. The extract of the *Eriobotrya japonica* Lindl. leaf cells obtained by the steps described above substantially contained no components soluble in 50 vol % methanol and insoluble in 85 vol % methanol.

(6) Purification of Tormentic Acid

About 1 g white powder of the extract of the *Eriobotrya japonica* Lindl. leaf cells was placed on a silica gel (LiChroprep RP-18, E. Merck, 40 to 63 µm), and was purified by a preparative high performance liquid chromatograph (HPLC, pump: Shimadzu LC-8A (Kyodo, Japan); mobile phase: 85 vol % methanol; flow rate: 3 ml/min; column: YMC, J' Sphere series ODS-H80 column (internal diameter: 10 mm; length: 250 mm; particle size: 5 µm) with partition by a methanol to water ratio of from 8:2 to 10:0 to obtain tormentic acid.

The purified compound was analyzed by mass spectrometry (purchased from Jeol GCmate, Tokyo, Japan) and NMR ($^1$H, $^{13}$C, DEPT, COSY, HMQC, HMBC, Jeol 500 MHz, Tokyo, Japan), and the main component was recognized as tormentic acid (the compound of formula (1)).

(1)

Tormentic acid (25.3 mg): $^1$H-NMR (pyridine-$d_5$): δ 0.92 (3H, s, H-24), δ 1.00 (3H, s, H-25), δ 1.12 (3H, s, H-26), δ 1.12 (3H, s, H-30), δ 1.28 (3H, s, H-23), δ 1.43 (3H, s, H-29), δ 1.65 (3H, s, H-27), 1.74 (1H, t, J=12.7 Hz, H-1), 1.90 (1H, dd, J=12.0, 3.8 Hz, H-1), 2.34 (1H, td, J=13.2, 4.1 Hz, H-15), δ 3.05 (3H, s, H-18), δ 3.14 (1H, td, J=13.1, 4.1 Hz, H-16), δ 3.77 (3H, s, H-3), δ 4.31 (1H, dt, J=10, 2.6 Hz, H-2), δ 5.59 (1H, s, H-12). $^{13}$C-NMR (pyridine-$d_5$): δ17.1 (C-30), 17.2 (C-25), 19.1 (C-6), 22.8 (C-24), 17.7 (C-26), 24.5 (C-11), 25.1 (C-27), 26.9 (C-16), 27.4 (C-21), 27.6 (C-29), 29.7 (2C, C-15, C-23), 34.0 (C-7), 39.0 (C-22), 39.1 (C-10), 39.3 (C-4), 41.1 (C-8), 42.6 (C-1), 42.8 (C-20), 43.3 (C-14), 48.1 (C-9), 48.7 (C-17), 49.2 (C-5), 55.1 (C-18), 66.6 (C-2), 73.2 (C-19), 79.8 (C-3), 128.5 (C-12), 140.4 (C-13), 181.2 (C-28).

(7) Determination of the Content of Tormentic Acid

Figure 1:
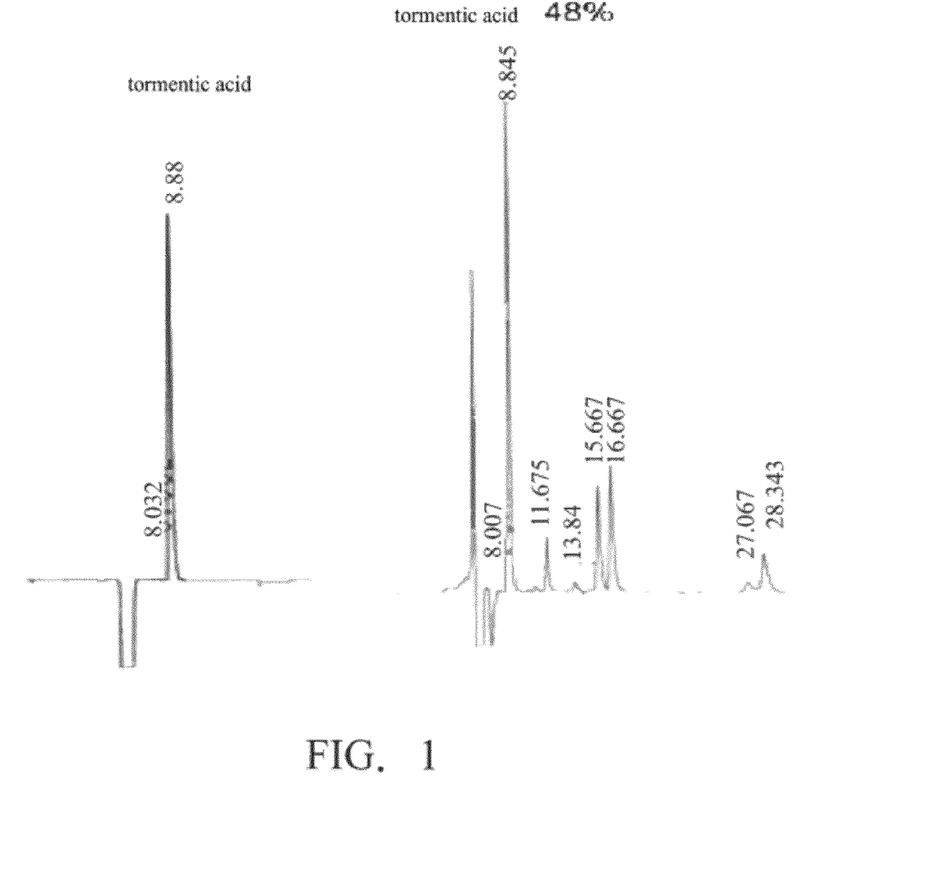
FIG. 1 is an HPLC chromatogram of tormentic acid in the *Eriobotrya japonica* Lindl. leaf cell extract.

The content of tormentic acid was determined by HPLC. The used conditions for HPLC were as follows: the pump was Shimadzu LC-10ATvp; the refractive index detector was Shimadzu RID-10A; HyPURITY C-18 column (internal diameter: 4.6 mm; length: 250 mm; particle size: 5 µm); solvent system was methanol/0.15 vol % water-containing acetic acid at a volume ratio of 85:15; flow rate was 0.5 ml/min; temperature was 35° C. As shown in FIG. 1, the content of tormentic acid was about 48 wt % based on the dry weight of the extract of the *Eriobotrya japonica* Lindl. leaf cells.

Example 2

Inhibition Test of the Matrix Metalloproteinase Activity

In addition to collagen decomposing, matrix metalloproteinase (collagenase) has the effect of gelatin decomposing. The property of the fluorescence generation of decomposed gelatin and decomposed commercial substrates of collagenase (purchased from Calbiochem, la Jolla, Canada) was used in this example to evaluate the inhibitory effect of tormentic acid on the matrix metalloproteinase.

Experiment A. Decomposition Test of Gelatin

A 50 µl buffer solution (pH 7.8, contained 50 mM Tris-HCl, 10 mM calcium chloride, and 0.15 M sodium chloride), 30 µl sterile water, and 10 µl bacterial matrix metalloproteinase (0.1 mg/ml, Sigma) were added into an eppendorf tube, and then a 10 µl solution of tormentic acid (dissolved in dimethyl sulfoxide) of various concentrations (25, 50, 100, or 200 mg/ml) or doxycycline as the positive control was added into the eppendorf tube. The mixture was well mixed, and incubated at room temperature for 60 minutes.

The mixture (30 µl) was drawn and dropped on a circular filter paper covering a gelatin culture medium, and then the filter paper along with the medium was placed into an incubator under 37° C. After incubating for 18 hours, the filter paper was removed. The culture medium was stained with a Coomassie Blue R-250 staining solution (purchased from Amresco company, America), and then was destained with a destaining solution. Because gelatin decomposed by matrix metalloproteinase will not be stained by the Coomassie Blue staining solution, the transparency of the culture medium may reveal the activity of the matrix metalloproteinase. After the culture medium was photographed, the picture was analyzed by an image analysis software (AlphaDigiDoc 1201, purchased from Alpha Innotech Co., America) to calculate the inhibition rate of tormentic acid on the activity of gelatin decomposition of the matrix metalloproteinase. The testing results are shown in Table 1 and FIG. 2.

TABLE 1

| | Concentration (µg/ml) | Inhibition rate (%) |
|---|---|---|
| control | — | 0.0 |
| doxycycline | 500 | 55.0 |
| tormentic acid | 25 | 3.7 |
| tormentic acid | 50 | 24.0 |
| tormentic acid | 100 | 62.7 |
| tormentic acid | 200 | 75.3 |

Figure 2:
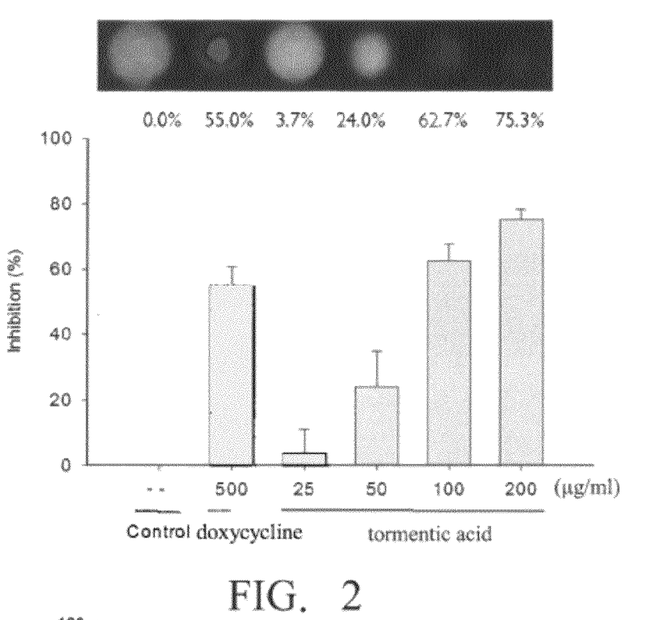
FIG. 2 is a staining picture and a column diagram showing the inhibition rate of tormentic acid on gelatin decomposing activity of MMP.

As shown in Table 1 and FIG. 2, tormentic acid significantly inhibited the activity of gelatin decomposition of the matrix metalloproteinase.

Experiment B. Fluorogenic Substrate Test

A specific amount of a solution of the collagenase substrate III (Mcc-Pro-Leu-Gly-Pro-D-Lys (DNP)—OH, purchased from Calbiochem, la Jolla, Canada), a matrix metalloproteinase (collagenase, Sigma) solution, tormentic acid or doxycycline as the positive control were mixed and added to a 96 well plate. Then, an ELISA reader was used to determine the absorption values of the mixture under luminescence excitation light (285 nm) and radioactive light (405 nm), respectively. The results are shown in Table 2 and FIG. 3, wherein ΔF is the fluorescence value that the basic fluorescence value at time zero has been deducted.

TABLE 2

| | Concentration (µg/ml) | ΔF (Inhibition rate) | |
|---|---|---|---|
| control | — | 90.0 ± 7.6 | |
| doxycycline | 250 | 27.9 ± 3.7*** | (69%) |
| doxycycline | 500 | 0 ± 0*** | (100%) |
| tormentic acid | 50 | 54.8 ± 8.4*** | (39%) |
| tormentic acid | 100 | 49.8 ± 7.2*** | (44.7%) |
| tormentic acid | 250 | 18.8 ± 10.8*** | (79.1%) |

Figure 3:
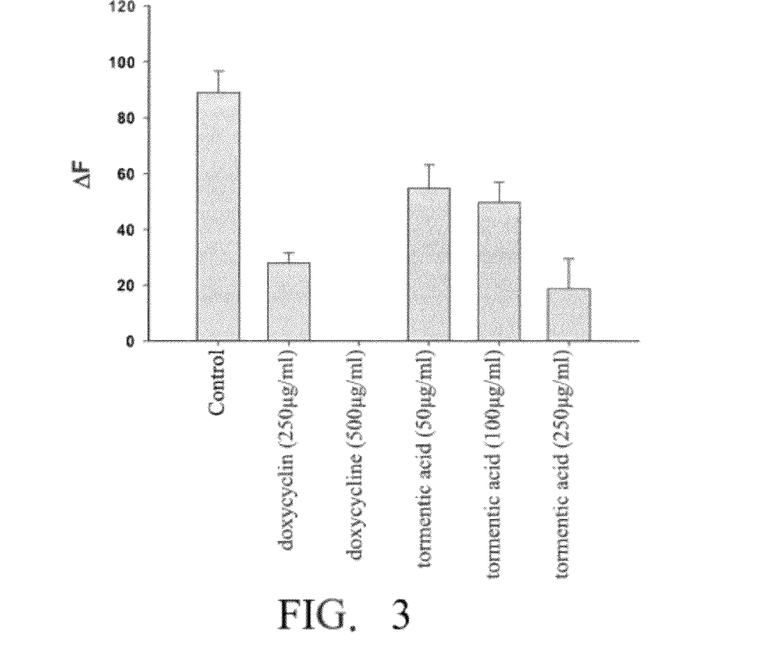
FIG. 3 is a column diagram showing the inhibition rate of tormentic acid on the collagenase substrate decomposing activity of MMP.

Table 2 and FIG. 3 show that tormentic acid can reduce the generation of fluorescence, illustrating that tormentic acid can inhibit the activity of the matrix metalloproteinase for the decomposition of the collagenase substrate III.

The results of Experiment A and Experiment B indicate that the pharmaceutical composition and the method of the present invention can inhibit the activity of the matrix metalloproteinase.

Example 3

Cell Test

Example C. Test of Cell Survival Rate

The following experiment was carried out by using WS1 human skin dermal fibroblasts (purchased from Food Industry Research and Development Institute, Taiwan). Under exposure to the ultraviolet ray (UV) with the intensity range from 0 mJ/cm$^2$ to 120 mJ/cm$^2$, it will not cause death to WS1 human skin dermal fibroblasts. Thus, this experiment was carried out at the UV intensity of 90 mJ/cm$^2$. First, tormentic acid of various concentrations (0, 0.1, 1.0, 2.0, or 10 μg/ml) was added to a culture medium (comprising α-minimum essential medium, 10% heat-inactivated Fetal Bovine Serum, 100 U/ml penicillin, and 100 μg/ml Streptomycin) containing the WS1 human skin dermal fibroblasts. After the cells were cultured for 24 hours, an MTS (3-(4,5-di-methylthiazol-2-yl)-5-(3-carboxymethoxy phenyl)-2-(4-sulfophenyl)-2H-tetrazolium, commercially available from Promega, Madison, Wis., America) assay was carried out to observe the cell survival rate, and the results are shown in Table 3. The mechanism of the MTS assay is as follows: the dehydrogenase activity of living cells can reduce MTS to a water soluble product that is red purple in color, which has a maximum absorption at a wavelength of 490 nm, and thus, the cell survival rate can be evaluated by absorption values.

TABLE 3

| | dosage of tormentic acid (μg/ml) | absorption value | survival rate (%) |
| --- | --- | --- | --- |
| UV exposure | 0 | 1.04 ± 0.91 | 100 |
| UV exposure + tormentic acid | 0.1 | 1.08 ± 0.95 | 103.8 |
| UV exposure + tormentic acid | 1.0 | 1.10 ± 0.97 | 105.8 |
| UV exposure + tormentic acid | 2.0 | 1.10 ± 0.98 | 105.8 |
| UV exposure + tormentic acid | 10.0 | 0.83 ± 0.70 | 79.8 |

As shown in Table 3, when the cells were exposed to 90 mJ/cm$^2$ UV, tormentic acid caused the death of the cells at a concentration of 10 μg/ml; but it did not cause the death of the cells under a concentration of lower than 2 μg/ml. This experiment shows that tormentic acid has no cytotoxicity under a low concentration.

Experiment D. Analysis of Procollagen-1 and Matrix Metalloproteinase-1

Figure 4:
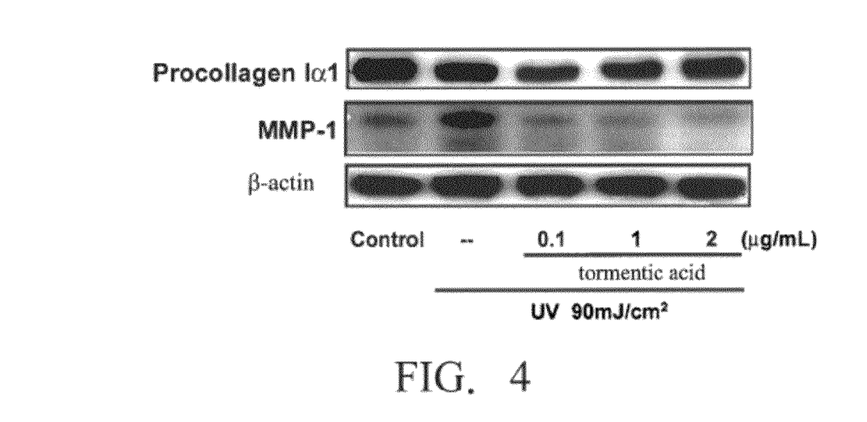
FIG. 4 is a protein electrophoresis picture of procollagen-1 and MMP-1 in WS1 human skin dermal fibroblasts.

Proteins in the WS1 human skin dermal fibroblasts in Experiment C were collected, and a western blotting assay was carried out to observe the protein expression level in the fibroblasts; the result is shown in FIG. 4. After the cells were exposed to UV for 24 hours, the expression of procollagen-1 in the WS1 human skin dermal fibroblasts was reduced, and the expression of matrix metalloproteinase-1 was increased. However, when the cells were treated with tormentic acid for 1 hour before collection, the expression of matrix metalloproteinase-1 was inhibited, and the expression of procollagen-1 was increased.

This example suggests that the pharmaceutical composition and the method of the present invention have the effects of inhibiting the expression of matrix metalloproteinase-1 and promoting the expression of collagen.

Experiment E. Analysis of the Phosphorylation of Mitogen-Activated Protein Kinase The skin "photo-aging" caused by ultraviolet rays may lead to an increase of matrix metalloproteinase in the dermis via the phosphorylation of the mitogen-activated protein kinase (MAPK), and thus a western blotting assay was also carried out in this experiment to observe the effect of tormentic acid on the phosphorylation of mitogen-activated protein kinase in cells; the result is shown in FIG. 5.

Figure 5:
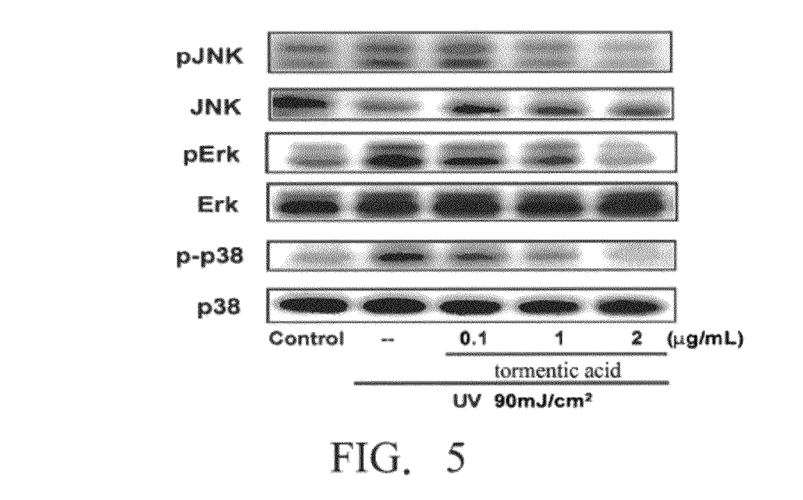
FIG. 5 is a protein electrophoresis picture of unphosphorylated and phosphorylated mitogen-activated protein kinase (JNK, ERK, and P38 protein) in WS1 human skin dermal fibroblasts.

As shown in FIG. 5, after the WS1 human skin dermal fibroblasts were exposed to UV rays for 24 hours, the expression of phosphorylated proteins of three kinds of mitogen-activated protein kinases (c-Jun N-terminal Kinase (JNK), extracellular signal-regulated protein kinase (ERK), and p38 protein) were increased. However, when the cells were treated with tormentic acid for 1 hour before collection, the phosphorylation of JNK, ERK, and p38 can be inhibited.

This example suggests that the pharmaceutical composition and the method of the present invention have the effects of inhibiting the expression of matrix metalloproteinase-1 via the inhibition of the mitogen-activated protein kinase (MAPK) pathway, thereby promoting the expression of collagen.

Figure 6:
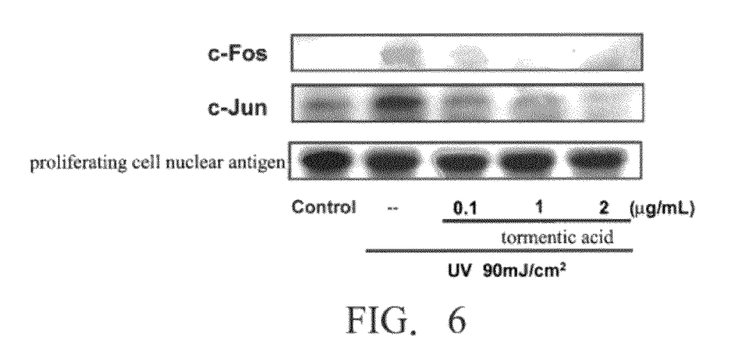
FIG. 6 is a protein electrophoresis picture of AP-1 in the nuclei of WS1 human skin dermal fibroblasts.

Experiment F. Analysis of the Expression of Activator Protein 1 Gene Transcription Factor The UV exposure of cells induces JNK and p38 to activate c-Jun, which then enters into the nucleus. Then, c-Fos translocates into the nucleus under the regulation of ERK and p38. A c-Jun subunit combines with a c-Fos subunit to form an activator protein 1 (AP-1) gene transcription factor, which then participates in gene expression to promote the transcription of message RNA (mRNA) of matrix metalloproteinase-1 (MMP-1) and reduces the gene expression of procollagen-Iα1 (procollagen α1 of Type I collagen). Thus, a western blotting assay was carried out in this experiment to further observe the protein expression of AP-1 in the nucleus, and the result is shown in FIG. 6. After the WS1 human skin dermal fibroblasts were exposed to UV rays for 24 hours, the expression level of c-Jun and c-Fos in the nucleus were increased. However, when the cells were treated with tormentic acid for 1 hour before collection, the expression of c-Jun and c-Fos were inhibited.

This example suggests that the pharmaceutical composition and the method of the present invention has the effect of inhibiting the translocation of AP-1 into the nucleus via the inhibition of the phosphorylation of mitogen-activated protein kinase induced by UV exposure, thereby inhibiting the gene transcription of MMP-1 and procollagen-Iα1.

Example 4

Animal Test

Experiment G. Analysis of the Skin Wrinkling

The following experiment was carried out by using 7-week-old SKH-1 hairless male mice (purchased from Charles river Lab, America). The mice were placed into 2 groups: a control group (6 mice) and a UVB (medium wavelength UV) group (24 mice). The mice of the UVB group were exposed to UVB three times a week (i.e., Monday, Wednesday, and Friday). The intensity of UVB exposure in the first week was 90 mJ/cm$^2$, and in the $2^{nd}$ to $12^{th}$ weeks were 120 mJ/cm$^2$.

The UVB group was further classified into three groups of eight. The three groups were, respectively, 1) exposed to UVB only (hereinafter referred to as "UVB group"), 2) exposed to UVB and applied with a cream vehicle (hereinafter referred to as "vehicle group", wherein the vehicle comprises a 0.5 wt % *Pueraria mirifica* extract, 5 wt % squalane, 2 wt % sodium ascorbyl phosphate, 5 wt % 1,3-butylene glycol, 2 wt % dipropylene glycol, 3 wt % polyethylene glycol 400, 0.5 wt % xanthan gum, 5 wt % glycerol, and 77 wt % pure water), and 3) exposed to UVB and applied with cream containing 0.5 wt % *Eriobotrya japonica* Lindl. leaf cell extract (containing tormentic acid and hereinafter referred to as "extract group"). After the UVB exposure was done in the vehicle group and extract group, 0.2 ml vehicle emulsion or cream containing 0.5 wt % *Eriobotrya japonica* Lindl. leaf cell extract was applied to the back of the mice immediately, respectively.

The thickness of the skin of the mice was measured on the next to last day of UVB exposure, and the skin of the mice was observed and photographed. The degree of skin wrinkling was scaled into four levels (0, 2, 4, and 6) according to Bissett's evaluation method (which can be seen in Kim et al., Effects of ginseng saponins isolated from red ginseng on ultraviolet B-induced skin aging in hairless mice, *Eur J Pharmacol.* 2009; 602:148-156, which is entirely incorporated hereinto by reference). The result is shown in FIG. 7.

Figure 7:
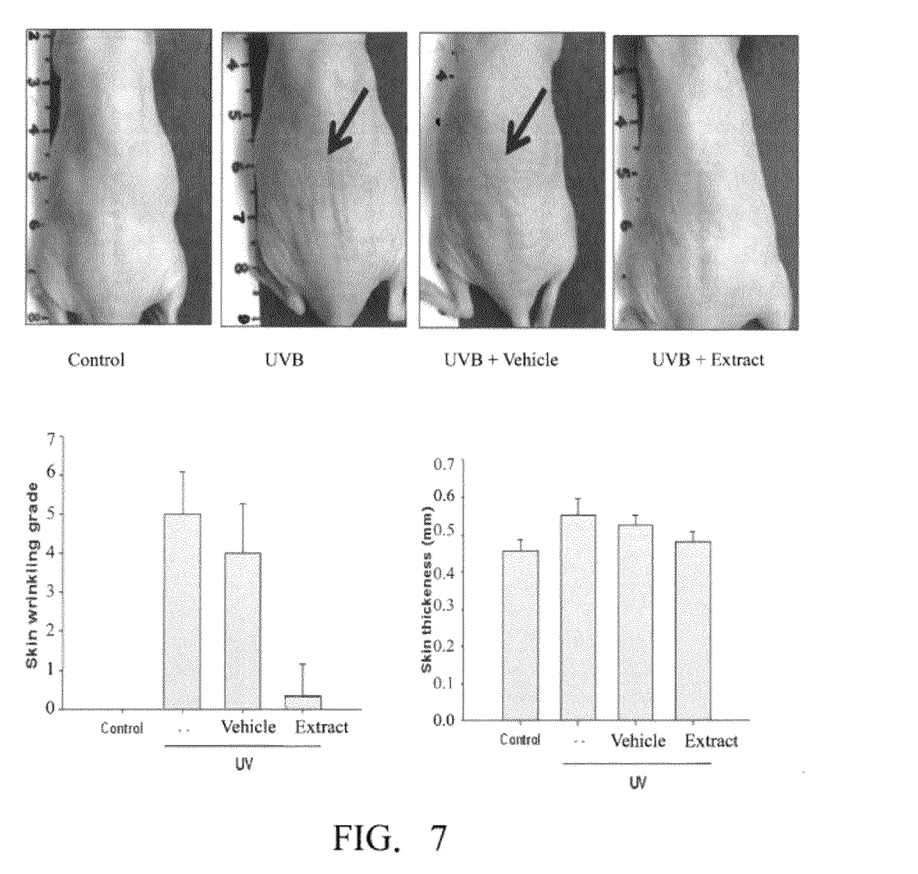
FIG. 7 is a picture and a column diagram showing the variety of skin thickness and wrinkle formation of the mice exposed to UVB.

As shown in FIG. 7, compared with the control group without UVB exposure, after the mice were exposed to UVB for 12 weeks, the back skin of the mice was thicker, and the wrinkles were apparent. The level of the skin thickness and wrinkle formation of the mice in the extract group was significantly slighter than the mice of the UVB group, and there was no apparent improvement in the vehicle group. This example suggests that tormentic acid has the effect of anti-photo-aging on skin.

Experiment H. Histological Staining—Analysis of the Epidermis, Dermis, and Collagen After the analysis of the skin wrinkling was finished, the mice were anaesthetized by $CO_2$ inhalation and sacrificed, and the back skin of the mice was removed and divided into six pieces. One piece of the back skin was soaked in a 30 wt % sugar solution for frozen section; another piece was soaked in a 10 wt % formalin solution for paraffin section; the other four pieces were collected in zipper bags, labeled respectively, and stored at −80° C.

Figure 8:
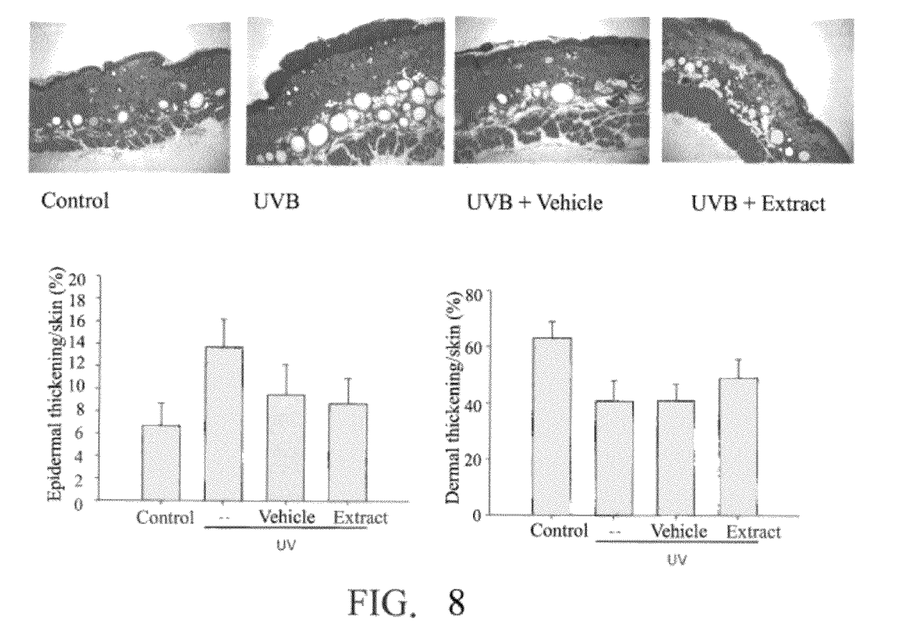
FIG. 8 is a staining picture and a column diagram showing the variety of the thickness of the epidermis and dermis of the mice exposed to UVB.

The piece of skin soaked in the 10 wt % formalin solution for one week was taken for paraffin embedding and slicing, and the slices were then stained by two methods. The first method was a general staining of hematoxylin and eosin stain (HE stain), while the other was a special staining for collagen (i.e., Sirius Red stain). Ten image blocks in each image file of the HE stained slices of each mouse were selected randomly, and were analyzed by an image analysis software (Image-Pro Plus 5.1, purchased from Media Cybernetics, MD, America) to obtain the thickness of the epidermis and dermis. Then, the ratio of the thickness of the epidermis or dermis to the entire skin thickness was calculated, and the results are shown in FIG. 8. On the other hand, the ratio of collagen of the Sirius Red stained slices to the entire skin was analyzed and calculated, and the results are shown in FIG. 9.

As shown in FIG. 8, compared with the control group without UVB exposure, the results of the HE stain show that the thickness of the epidermis of the mice exposed to UVB for 12 weeks was significantly increased, and the thickness of the dermis was significantly decreased. However, the thickness of the epidermis of the mice applied with the *Eriobotrya japonica* Lindl. leaf cell extract was decreased, and the thickness of the dermis was increased. Furthermore, the thickness of the epidermis of the mice in the vehicle group was decreased, but the thickness of the dermis was not affected.

Figure 9:
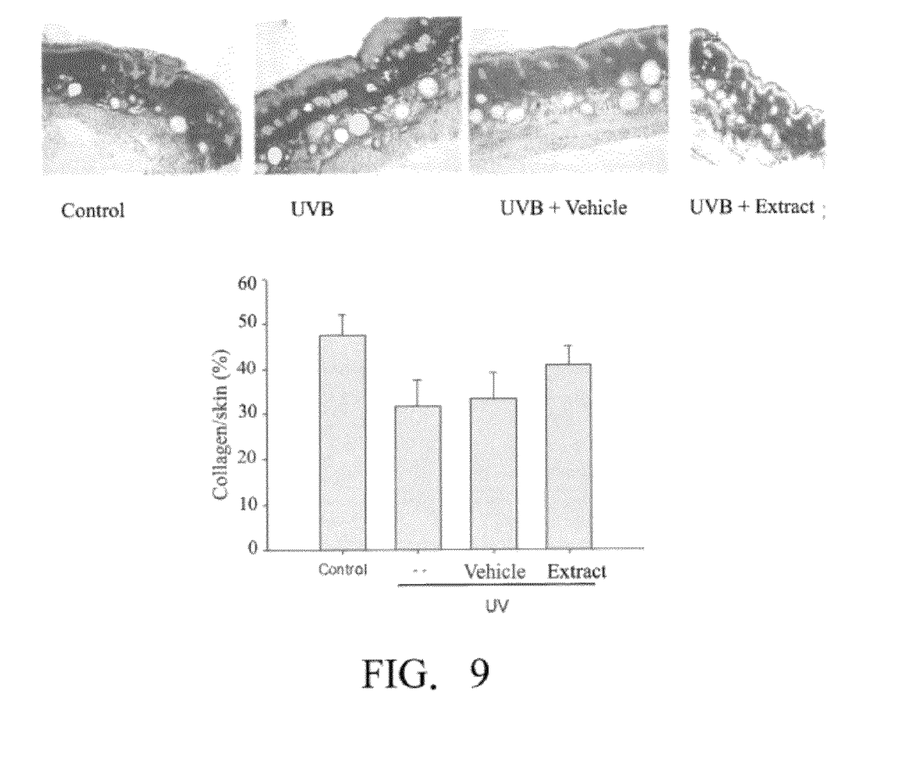
FIG. 9 is a staining picture and a column diagram showing the variety of the ratio of collagen to the entire area of the dermis of the mice exposed to UVB.

As shown in FIG. 9, compared with the control group without UVB exposure, the results of the Sirius Red stain show that collagen in the back skin of the mice exposed to UVB for 12 weeks was significantly decreased, while the collagen in the skin of the mice in the extract group was significantly greater than that of the mice in the UVB group. There was no apparent improvement in the vehicle group.

The result of Example H suggests that the pharmaceutical composition and the method of the present invention have the effect of increasing the collagen content in the dermis of the skin.

Experiment I. Histological Staining—Analysis of Matrix Metalloproteinase-1

The skin tissues soaked in the 30 wt % sugar solution for 24 hours in Experiment H were taken for frozen section. The skin tissues were frozen and embedded in a tissue freezing medium, and stored at −80° C. Before staining, a skin tissue sample with a thickness of 6 µm was cut from the tissues by a freezing microtome (Leica CM3050S, purchased from Leica company, Germany). Furthermore, the sample was affixed to a microslide, and fixed with ice-acetone at room temperature for 10 minutes. Then, the immunohistochemical fluorescence staining of MMP-1 and the immunostaining and hydrogen peroxide staining of COX-2 (cyclooxygenase-2) were performed.

The immunohistochemical fluorescence staining of MMP-1 was carried out by the following process. First, the frozen section was rinsed with a phosphate buffered saline (PBS) solution three times, soaked in 5 wt % milk for reaction for 30 minutes, and was rinsed with PBS for another three times. Then, an anti-MMP-1 antibody (purchased from Santa Cruz) was added to the section, and the section was covered in paraffin, placed in a wet box at 4° C. overnight, and then rinsed with PBS for three times. Furthermore, a fluorescent secondary antibody (Alexa Fluor® 488 goat anti-rabbit IgG (H+L), purchased from Invitrogen) was added to the section, and then the section was covered with parafilm, put in a wet box, and stored in darkness at the room temperature for 45 minutes. Then, the section was rinsed with PBS for three times, covered with a cover glass in wet state to avoid air bubble entrapment, and immediately photographed by fluorescent microscopy. Finally, the ratio of the MMP-1 to the entire area of the skin was analyzed by an image analysis software, and the result is shown in FIG. 10.

Figure 10:
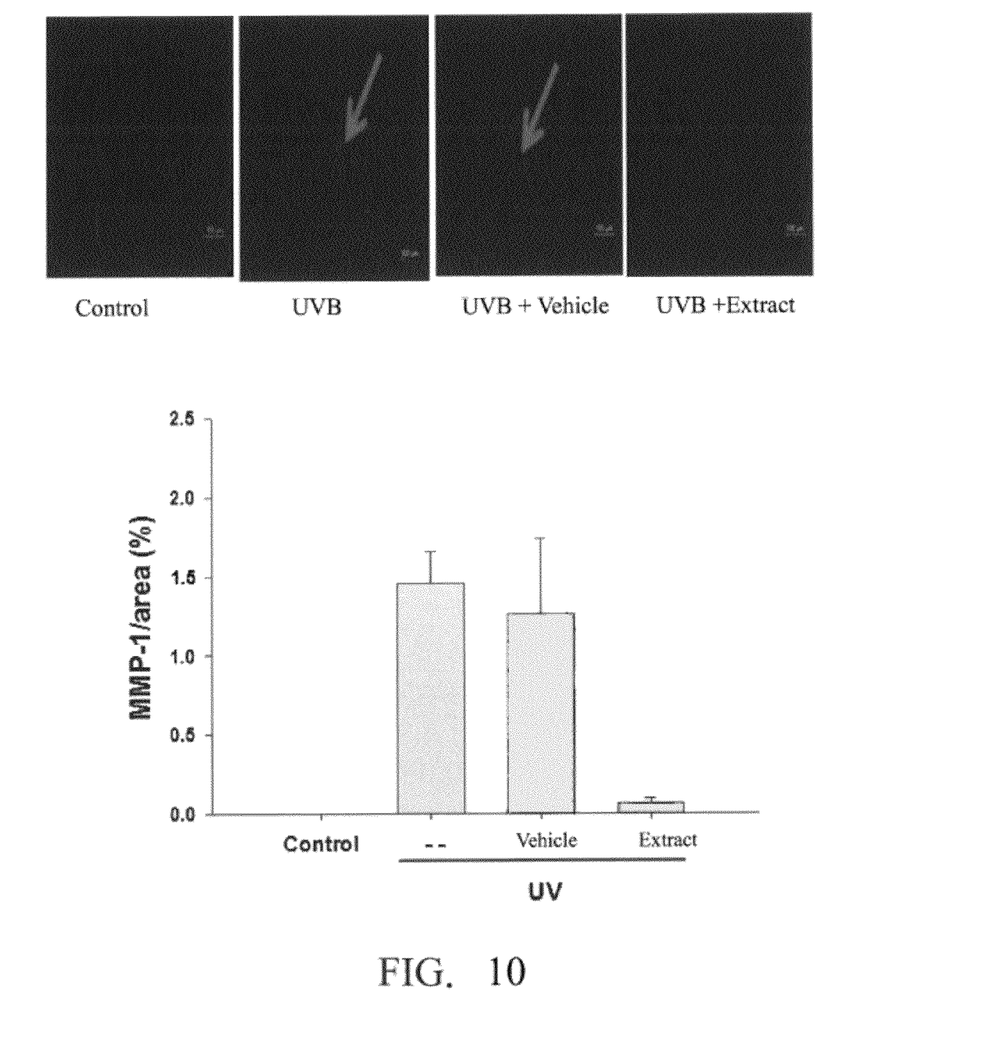
FIG. 10 is a staining picture and a column diagram showing the variety of the ratio of MMP-1 to the entire area of the skin of the mice exposed to UVB.

As shown in FIG. 10, compared with the control group without UVB exposure, MMP-1 in the back skin of the mice exposed to UVB for 12 weeks was significantly increased, but the expression of MMP-1 of the mice in the extract group was lower than that of the UVB group. Because there was no apparent improvement in the vehicle group, this suggests that the effect of anti-aging of skin was mainly from the *Eriobotrya japonica* Lindl. leaf cell extract.

Experiment J. Histological Staining—Analysis of Anti-Inflammatory

COX-2 Immunostaining comprises the following steps. First, the frozen section in Experiment H was rinsed with PBS three times, and soaked in 0.3 wt % hydrogen peroxide/PBS. Second, the section was rinsed with PBS slightly after being placed at room temperature for 10 minutes. Then, the section was soaked in a blocking buffer and placed at room temperature for 30 minutes, and rinsed with PBS for three times. An anti-COX-2 primary antibody (purchased from Cell Signaling) was added to the section, and the section was covered in parafilm, put in a wet box at 4° C. overnight, and rinsed with PBS three times. Furthermore, a secondary antibody was added to the section at room temperature for reaction for 30 minutes. Finally, an immunodetection kit (purchased from BioGenex, San Ramon, Canada) and diaminobenzidine (DAB) was used for color reaction, and the section was stained with hematoxylin. Then, the section was dehydrated and sealed, and the result is shown in FIG. 11.

Figure 11:
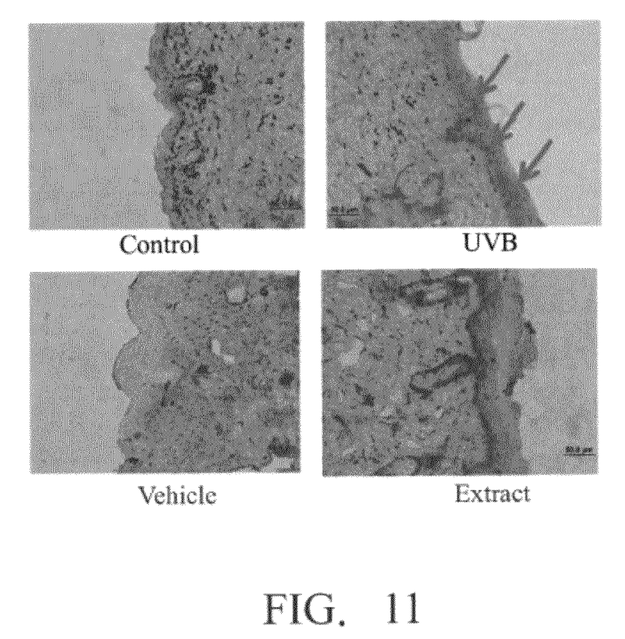
FIG. 11 is a staining picture showing the variety of COX-2 in the skin of the mice exposed to UVB.

As shown in FIG. 11, compared with the control group without UVB exposure, the expression of COX-2 in the back skin of the mice exposed to UVB for 12 weeks was significantly increased. The expression of the COX-2 of the mice in the extract group was lower than that in the UVB group. There was no apparent improvement in the vehicle group. These results suggest that the *Eriobotrya japonica* Lindl. leaf cell extract containing tormentic acid can achieve the effect of anti-aging of skin via anti-inflammation.

Experiment K. Histological Staining—Analysis of Anti-Oxidation

The hydrogen peroxide staining of the section was performed according to the method of Dannenberg et al (which can be seen in Dannenberg et al., Histochemical demonstration of hydrogen peroxide production by leukocytes in fixed-frozen tissue sections of inflammatory lesions. *J Leukoc Biol.* 1994; 5:436-43, which is entirely incorporated hereinto by reference). First, the frozen section in Experiment F was soaked in a 0.1 M Tris-HCl buffer (pH 7.5) containing 1 mg/ml glucose and 1 mg/ml diamino benzidine, and placed in an incubator under 37° C. for 6 hours. Then, the section was rinsed with PBS for three times, and stained with hematoxylin. After slightly rinsing with PBS, the section was covered with a cover glass in the wet state to avoid air bubble entrapment, and photographed immediately by microscopy. The ratio of hydrogen peroxide to the entire area of the skin was analyzed by an image analysis software, and the result is shown in FIG. 12.

Figure 12:
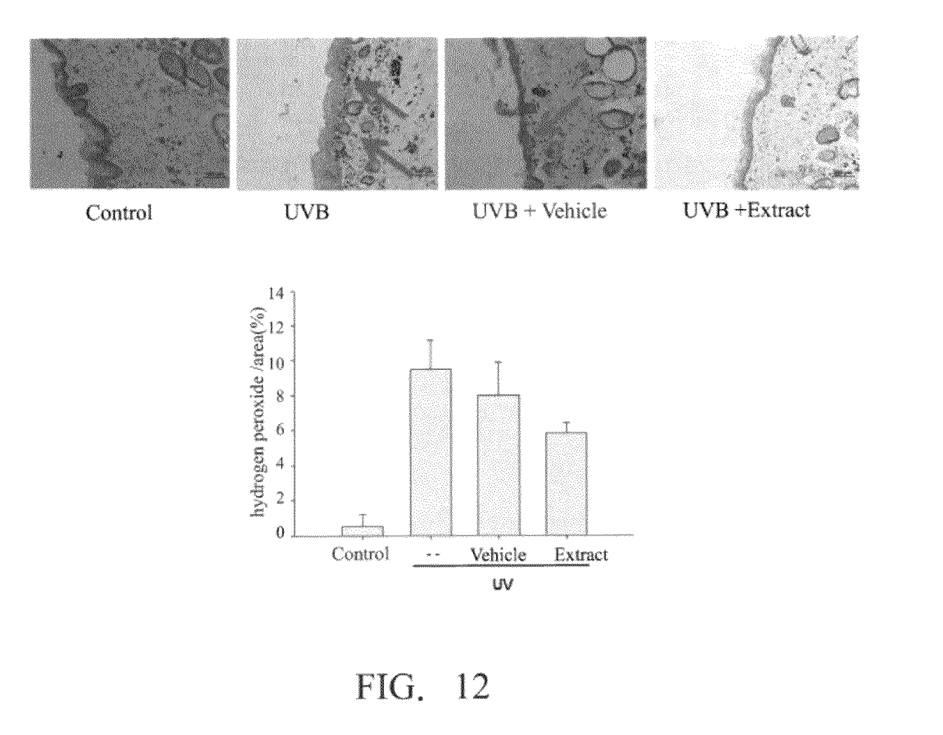
FIG. 12 is a staining picture and a column diagram showing the variety of the ratio of hydrogen peroxide to the entire area of the skin of the mice exposed to UVB.

As shown in FIG. 12, compared with the control group without UVB exposure, hydrogen peroxide in the back skin of the mice exposed to UVB for 12 weeks was significantly increased. The expression of hydrogen peroxide of the mice in the extract group was lower than that in the UVB group. There was no apparent improvement in the vehicle group. These results suggest that the *Eriobotrya japonica* Lindl. leaf cell extract containing tormentic acid can achieve the effect of anti-aging of skin via reducing the damage of oxidative stress.

The above examples show that the pharmaceutical composition and the method of the present invention have the effects of improvement, repair, and/or care of skin.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for treating skin photo-aging in a mammal, the method consisting of administering to the mammal, together with a pharmaceutically acceptable excipient, an effective amount of an active component selected from a group consisting of a compound of formula (I), a pharmaceutically acceptable salt of the compound, a pharmaceutically acceptable ester of the compound, and combinations thereof:

2. The method as claimed in claim 1, which is for improving, repairing, and/or caring for skin.

3. The method as claimed in claim 1, which is for treating skin photo-aging caused by medium-wave ultraviolet rays (UVB).

4. The method as claimed in claim 1, wherein the active component is the compound of formula (I).

5. The method as claimed in claim 1, which is for inhibiting the activity of matrix metalloproteinase (MMP), inhibiting the expression of matrix metalloproteinase, inhibiting the phosphorylation of mitogen-activated protein kinase (MAPK) and/or promoting the expression of collagen in the mammal.

6. The method as claimed in claim 5, which is for inhibiting the activity of matrix metalloproteinase and/or inhibiting its expression, wherein the matrix metalloproteinase comprises matrix metalloproteinase-1 (MMP-1).

7. The method as claimed in claim 5, which is for inhibiting the phosphorylation of mitogen-activated protein kinase (MAPK), wherein the mitogen-activated protein kinase is selected from the group consisting of c-Jun N-terminal kinase (JNK), extracellular signal-regulated protein kinase (ERK), p38 protein, and combinations thereof.

8. The method as claimed in claim 5, which is for promoting the expression of collagen, wherein the collagen is Type I collagen.

9. A method for treating skin photo-aging in a mammal, the method consisting of administering to the mammal an effective amount of an active component selected from a group consisting of a purified compound of formula (I), a pharmaceutically acceptable salt of the purified compound, a pharmaceutically acceptable ester of the purified compound, and combinations thereof:

10. The method as claimed in claim 9, which is for improving, repairing, and/or caring for skin.

11. The method as claimed in claim 9, which is for treating skin photo-aging caused by medium-wave ultraviolet rays (UVB).

12. The method as claimed in claim 9, wherein the active component is the purified compound of formula (I).

13. The method as claimed in claim 9, which is for inhibiting the activity of matrix metalloproteinase (MMP), inhibiting the expression of matrix metalloproteinase, inhibiting the phosphorylation of mitogen-activated protein kinase (MAPK) and/or promoting the expression of collagen in the mammal.

14. The method as claimed in claim 13, which is for inhibiting the activity of matrix metalloproteinase and/or inhibiting its expression, wherein the matrix metalloproteinase comprises matrix metalloproteinase-1 (MMP-1).

15. The method as claimed in claim 13, which is for inhibiting the phosphorylation of mitogen-activated protein kinase (MAPK), wherein the mitogen-activated protein kinase is selected from the group consisting of c-Jun N-terminal kinase (JNK), extracellular signal-regulated protein kinase (ERK), p38 protein, and combinations thereof.

16. The method as claimed in claim 13, which is for promoting the expression of collagen, wherein the collagen is Type I collagen.

\* \* \* \* \*